(12) United States Patent
Masuda et al.

(10) Patent No.: US 10,101,283 B2
(45) Date of Patent: Oct. 16, 2018

(54) NUCLEAR MATERIAL DETECTION DEVICE AND NUCLEAR MATERIAL DETECTION METHOD

(71) Applicant: Kyoto University, Kyoto (JP)

(72) Inventors: Kai Masuda, Kyoto (JP); Tsuyoshi Misawa, Osaka (JP); Yoshiyuki Takahashi, Osaka (JP); Takahiro Yagi, Osaka (JP)

(73) Assignee: KYOTO UNIVERSITY, Kyoto (JP)

( * ) Notice: Subject to any disclaimer, the term of this patent is extended or adjusted under 35 U.S.C. 154(b) by 612 days.

(21) Appl. No.: 14/423,095

(22) PCT Filed: Aug. 28, 2013

(86) PCT No.: PCT/JP2013/073042
§ 371 (c)(1),
(2) Date: Feb. 20, 2015

(87) PCT Pub. No.: WO2014/034734
PCT Pub. Date: Mar. 6, 2014

(65) Prior Publication Data
US 2015/0192530 A1    Jul. 9, 2015

(30) Foreign Application Priority Data
Aug. 31, 2012 (JP) ................................ 2012-191500

(51) Int. Cl.
*G21B 1/00* (2006.01)
*H05H 1/22* (2006.01)
(Continued)

(52) U.S. Cl.
CPC ............. *G01N 23/025* (2013.01); *G01T 3/00* (2013.01); *G01T 3/06* (2013.01); *G01V 5/0091* (2013.01); *G01N 2223/626* (2013.01)

(58) Field of Classification Search
CPC .................................. G21B 1/00; H05H 1/22
(Continued)

(56) References Cited

U.S. PATENT DOCUMENTS

| 4,568,510 A | 2/1986 | Caldwell |
| 5,930,314 A * | 7/1999 | Lanza .................. G01N 23/204 |
| | | 250/358.1 |

(Continued)

FOREIGN PATENT DOCUMENTS

| EP | 2299295 A1 | 3/2011 |
| JP | 2003-315289 | 6/2003 |

(Continued)

OTHER PUBLICATIONS

Slaughter et al., "Detection of special nuclear material in cargo containers using neutron interrogation."*

(Continued)

*Primary Examiner* — Marshall P O'Connor
(74) *Attorney, Agent, or Firm* — Lewis Roca Rothgerber Christie LLP

(57) ABSTRACT

A nuclear material within a container is to be detected. Included are: a neutron source for generating neutrons emitted toward the container; a detection section capable of detecting neutrons including primary neutrons emitted from the neutron source and secondary neutrons generated through a nuclear fission reaction of the nuclear material; and a processing section for performing a reactor noise analysis process based on data obtained through detecting of neutrons by the detection section. The neutron source generates neutrons in a pulsatile manner. The processing section performs the reactor noise analysis process based on data obtained by excluding, from time series data obtained through detecting of neutrons by the detection section, data (Continued)

of a time range including a generation time of the neutrons generated by the neutron source in the pulsatile manner.

16 Claims, 14 Drawing Sheets

(51) Int. Cl.
    *G01N 23/02*     (2006.01)
    *G01T 3/00*     (2006.01)
    *G01T 3/06*     (2006.01)
    *G01V 5/00*     (2006.01)

(58) Field of Classification Search
    USPC .......................................................... 376/159
    See application file for complete search history.

(56) References Cited

U.S. PATENT DOCUMENTS

| | | | |
|---|---|---|---|
| 7,423,273 B2 * | 9/2008 | Clayton | G01N 23/04 250/358.1 |
| 2009/0065693 A1 | 3/2009 | Safa | |
| 2010/0046690 A1 | 2/2010 | Proctor et al. | |

FOREIGN PATENT DOCUMENTS

| | | |
|---|---|---|
| JP | 2008-503742 A | 2/2008 |
| WO | 01/84183 A2 | 11/2001 |

OTHER PUBLICATIONS

Hiroto Tsukazaki, Fujio Hiraga, Takashi Kamiyama, Yoshiaki Kiyanagi, "Study on Fissile Material Detection using D-T neutron for a freight container", Atomic Energy Society of Japan '2007 Nen Aki no Taikai' Yokoshu, Sep. 7, 2007 (Sep. 7, 2007), p. 168.

Michihiko Ito, Fujio Hiraga, Takashi Kamiyama, Yoshiaki Kiyanagi, "Influence of shields on nuclear material detection for cargo containers using pulsed neutron and γ-rays", Atomic Energy Society of Japan '2009 Nen Aki no Taikai' Yokoshu, Aug. 28, 2009 (Aug. 28, 2009), p. 369.

Taira Hazama, Tomoaki Mouri, Nagafumi Aihara, "Development Sub-Criticality Measurement Technique", JNC Technical Review, Mar. 2002, No. 14, pp. 115 to 123.

J.H. Sorebo, G.L. Kulcinski, R.F. Radel, J.F. Santarius, "Special Nuclear Materials Detection Using IEC Fusion Pulsed Neutron Source", Fusion Science and Technology 56 (2009) 540.

European Search Report, Application No. EP 13832574.1 dated Mar. 29, 2016 (8 pages).

Radel R. F., et al.: "Detection of Highly Enriched Uranium Using a Pulsed D-D Fusion Source", Fusion Science and Technology vol. 52, Nov. 2007, pp. 1087-1091.

PCT Application No. PCT/JP2013/073042 International Search Report and Written Opinion dated Oct. 8, 2013.

European Office Action dated Aug. 27, 2018 regarding European Patent Application No. EP 13 832 574.1 corresponding to U.S. Appl. No. 14/423,095 (7 pages).

Mihalczo et al., Physical description of nuclear materials identification system (NMIS) signatures, Nuclear Instruments & Methods in Physics Research. Section A, Elsevier BV * North-Holland, NL, vol. 450, No. 2-3, Aug. 11, 2000, pp. 532-555) XP004215590.

Hideaki et al., "Conceptual Design of a Nuclear Material Detection System Based on the Neutron/Gamma-ray Hybrid Approach,"Techonologies for Homeland Security (HST), 2010 IEEE International Conference on, IEEE, Piscataway, NJ, USA, Nov. 8, 2010, pp. 525-529, XP031815848, ISBN: 978-1-4244-6047-2.

Little et al., "Detection of Highly Enriched Uranium Through Active Interrogation," Jan. 1, 2006, XP55501052, Retrieved from the internet: URL:http://lxmi.mi.infn.it/~gladioli/Varenna2006/Proceedings/Little_R.pdf [retrieved on Aug. 21, 2018].

* cited by examiner

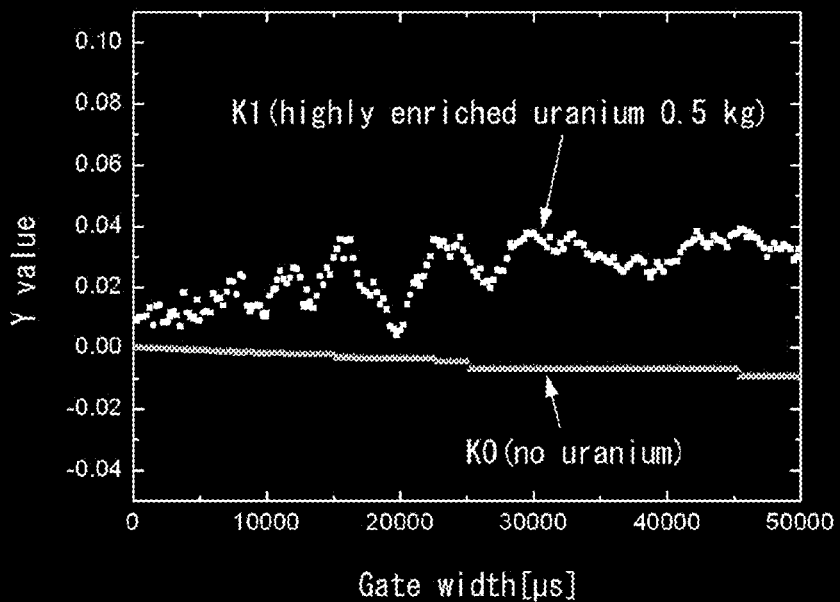
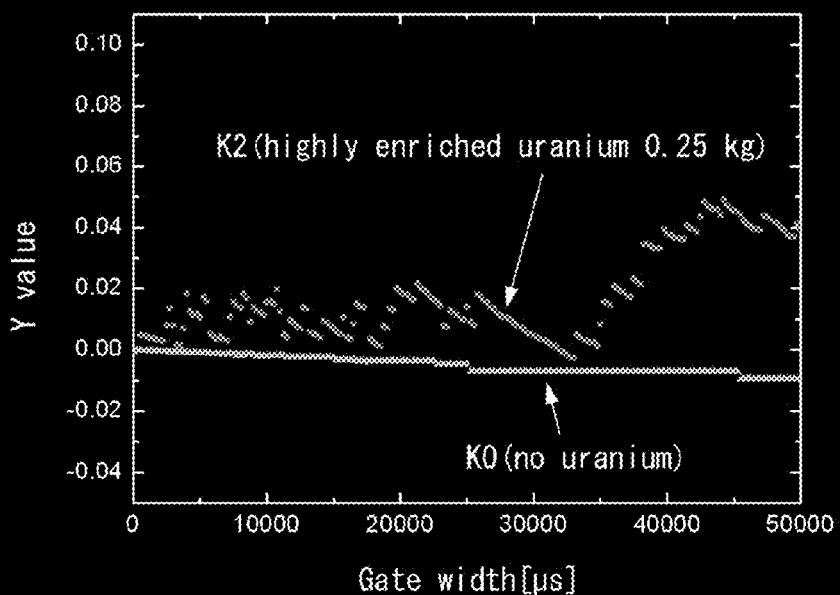
FIG. 7

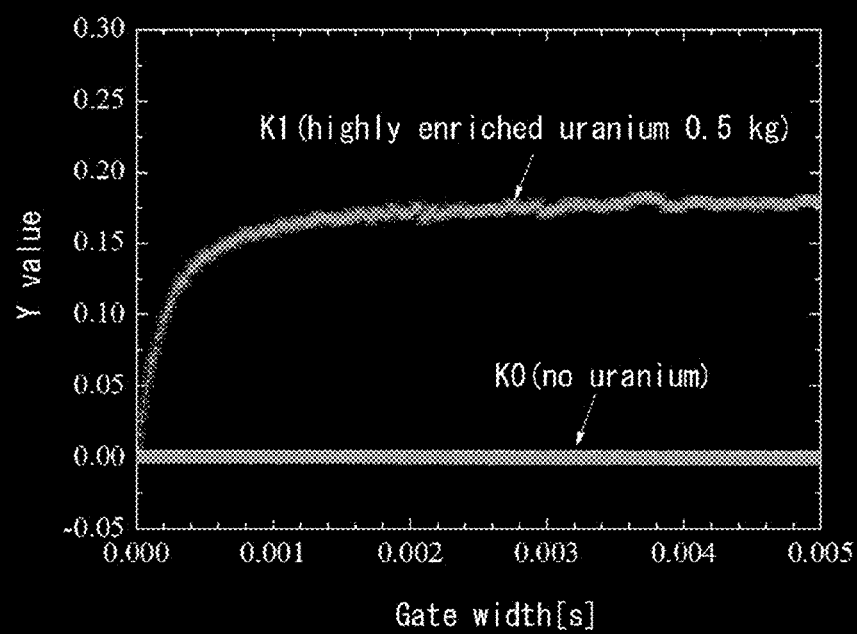

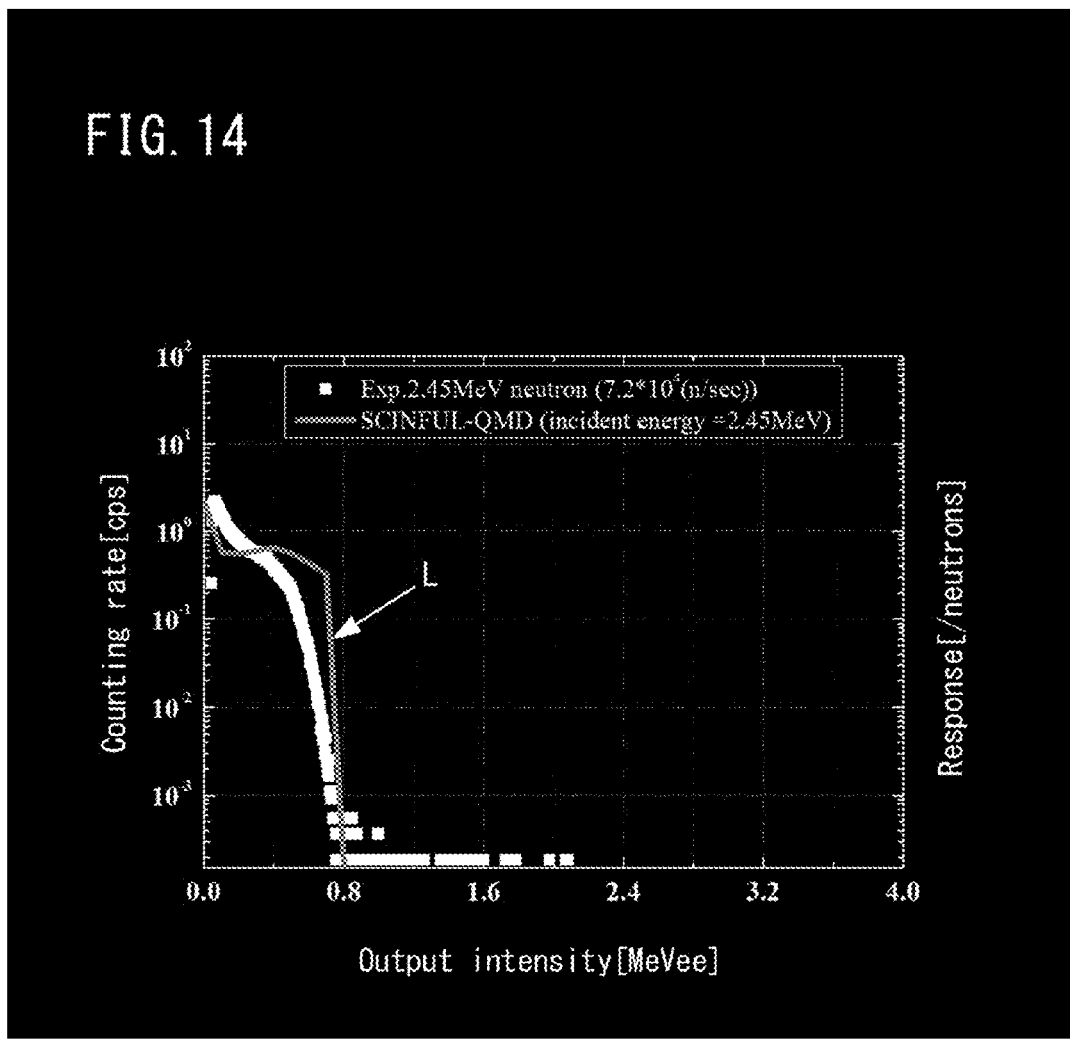

NUCLEAR MATERIAL DETECTION DEVICE AND NUCLEAR MATERIAL DETECTION METHOD

CROSS-REFERENCE TO RELATED APPLICATIONS

The present application is a national phase application of PCT application PCT/JP2013/073042 filed Aug. 28, 2013, which claims the priority benefit of Japanese patent application 2012-191500 filed Aug. 31, 2012, the disclosures of which are incorporated herein by reference.

BACKGROUND OF THE INVENTION

Technical Field

The present invention relates to a device and a method for detecting a nuclear material possibly concealed in a container or the like.

Background Art

The risk of terrorism using nuclear materials (special nuclear materials) such as uranium-235 and plutonium-239 has been increasing around the world. In order to prevent such terrorism beforehand, Megaports Initiative or the like in the United States has demanded development of technology for detecting a nuclear material concealed in a container or the like.

However, currently there are no technologies capable of performing, in a highly reliable manner, a non-destructive inspection using a simple device such as a portable type device on a container suspected to be concealing a nuclear material.

For example, conceivable means to detect a nuclear material includes a method of irradiating a container with strong radiation such as X-ray or the like and measuring neutrons and gamma rays generated from nuclear reactions of the nuclear material within the container. However, in such a case, a large size particle accelerator becomes necessary for generating the strong radiation, and it is extremely difficult to put such an accelerator to practical use as a portable device.

Patent Literature 1 discloses, as a small and simple inspection/analysis device utilizing neutrons, a device to inspect and analyze a sample by irradiating the sample (material) with neutrons generated through a fusion reaction, and using neutron scattering, neutron radiography, neutron-induced prompt gamma ray analysis, neutron activation analysis, or neutron reflective surface analysis.

CITATION LIST

Patent Literature

Patent Literature 1: Japanese Laid-Open Patent Publication No. 2003-315289

SUMMARY OF THE INVENTION

Technical Problem

In the device disclosed in Patent Literature 1, a technique is employed in which neutrons having a specific wavelength are extracted from the neutrons generated by a neutron source, the extracted neutrons having the specific wavelength are used for irradiating the sample, and neutrons scattered by the sample are detected.

However, detecting a nuclear material possibly concealed in a container or the like using such a technique is fundamentally not possible, and the technique cannot be put to practical use as a nuclear material detection device.

Thus, an object of the present invention is to provide a nuclear material detection device and a nuclear material detection method, which are highly capable of detecting a nuclear material and can be put to practical use.

Solution to Problem

The present invention is a nuclear material detection device for detecting a nuclear material within an object. The nuclear material detection device includes: a neutron source configured to generate neutrons used for irradiating the object; a detection section capable of detecting neutrons including primary neutrons emitted from the neutron source and secondary neutrons generated through a nuclear fission reaction of the nuclear material; and a processing section configured to perform a reactor noise analysis process based on data obtained through detecting of neutrons by the detection section. The neutron source generates neutrons in a pulsatile manner. The processing section performs the reactor noise analysis process based on data obtained by excluding data of a time range containing a generation time during which the neutron source generates the neutrons in the pulsatile manner, from time series data obtained through detecting of neutrons by the detection section.

The neutrons detected by the detection section include primary neutrons emitted from the neutron source, and, when a nuclear material is concealed within the object, secondary neutrons generated through a nuclear fission reaction of the nuclear material. Although detection of the secondary neutrons is necessary for detecting a nuclear material, the detection of the secondary neutrons becomes difficult because of the effect of the primary neutrons (i.e., the primary neutrons being the background).

Thus, in the present invention, neutrons (primary neutrons) are generated from the neutron source in a pulsatile manner, and a reactor noise analysis process of excluding data of a time range estimated to be largely affected by the primary neutrons, from time series data obtained through detecting of the neutrons by the detection section is performed. Thus, the capability to detect a nuclear material can be enhanced, and a nuclear material detection device that can be put to practical use can be obtained.

Furthermore, preferably, the processing section, in addition to generating the time series data, extracts data obtained by excluding data of the time range from the time series data, and performs the reactor noise analysis process based on the extracted data to obtain a noise component.

In this case, the data of the time range, in which the effect of the primary neutrons generated by the neutron source in the pulsatile manner is large, can be excluded from the time series data, and the data of the time range in which the effect of the primary neutrons is small can be extracted. Based on the extracted data of the time range, the reactor noise analysis process can be performed to obtain the noise component (Y value).

Furthermore, preferably, the processing section defines, as the time range, an interval from a generation start timing of the neutrons generated by the neutron source in the pulsatile manner to a timing after elapsing of a time period 500 to 5000 times of the generation time of the neutrons, and excludes the data of the time range from the time series data.

In this case, the effect of the primary neutrons generated by the neutron source in the pulsatile manner can be effectively excluded, and statistical error in the reactor noise analysis process can be reduced by reducing the amount of data excluded from the time series data.

Furthermore, preferably, the neutron source generates the neutrons using a fusion reaction of reacting two deuterium atoms.

When compared to a fusion reaction of reacting deuterium and tritium (hereinafter, also referred to as a DT fusion reaction), although the fusion reaction of reacting two deuterium atoms (hereinafter, also referred to as a DD fusion reaction) is inferior in terms of the amount of neutrons generated, a concealed nuclear material can be detected even when the DD fusion reaction is used as the neutron source since the capability to detect a nuclear material can be enhanced as described above. Furthermore, since tritium is not used in the DD fusion reaction, the device is safe and can be easily handled.

Furthermore, preferably, at least one of the neutron source and the detection section is mounted on a movable body that moves with respect to a road surface.

In order to mount the neutron source on the movable body, it is necessary to reduce the size of the neutron source. As described above, since the capability to detect a nuclear material can be enhanced, a small size neutron source is sufficient instead of a large size neutron source for generating a large amount of neutrons. As a result, mounting of the neutron source on the movable body becomes possible. In addition, since the capability to detect a nuclear material can be enhanced, the detection section can be reduced in size, and mounting of the detection section on the movable body becomes possible.

It should be noted that an automobile such as a truck or the like having a cargo bed can be used as the movable body, and at least one of the neutron source and the detection section can be mounted on the cargo bed.

Furthermore, it is possible to have a single movable body and mount both the neutron source and the detection section on this movable body, or have two movable bodies and mount the neutron source and the detection section on separate movable bodies.

Furthermore, a direction from the neutron source toward the object, and a direction from the object toward the detection section are preferably in an intersecting relationship.

In this case, neutrons emitted in the direction from the neutron source toward the object can be prevented from directly irradiating the detection section.

Furthermore, preferably: the neutron source is configured to generate neutrons using a fusion reaction of reacting two deuterium atoms; the detection section has a function of detecting a neutron together with an energy thereof; and the processing section has a function of determining that the neutrons detected by the detection section include a neutron having an energy higher than a maximum energy of the neutrons that have been generated through the fusion reaction and have reached the detection section.

In this case, when neutrons are generated from the neutron source using the fusion reaction of reacting two deuterium atoms (DD fusion reaction), the maximum energy of the primary neutrons reaching the detection section takes a certain value (2.45 MeV). On the other hand, the secondary neutrons generated from the nuclear material that is to be detected include a large amount of neutrons having an energy higher than the certain value (2.45 MeV). Thus, by setting, as a detection target, the neutrons having an energy higher than the maximum energy of the neutrons generated through the DD fusion reaction, the primary neutrons do not become a background, and the nuclear material can be determined to exist when a neutron having an energy higher than the maximum energy is detected.

Furthermore, it is possible to parallelly perform the detection (first detection process) of the nuclear material through the reactor noise analysis process, and the detection (second detection process) of the nuclear material based on detection of a neutron having an energy higher than the maximum energy. In this case, the reliability of detecting the nuclear material improves, since one of the detection processes functions as a backup of the other detection process, and the other detection process functions as a backup of the one of the detection processes.

Furthermore, the present invention is a nuclear material detection method for detecting a nuclear material within an object. The method includes: irradiating the object with neutrons in a pulsatile manner; detecting neutrons including primary neutrons used for the irradiating and secondary neutrons generated through a nuclear fission reaction of the nuclear material; and performing a reactor noise analysis process based on data obtained through the detecting. Here, the reactor noise analysis process is performed based on data obtained through exclusion of data of a time range that includes a generation time during which the neutrons are generated in the pulsatile manner, from time series data obtained through the detecting of neutrons.

With the present invention, operations and effects similar to those of the nuclear material detection device can be obtained.

It should be noted that the technology used for detecting a nuclear material in the nuclear material detection device and the nuclear material detection method of the present invention is not any of neutron scattering, neutron radiography, neutron-induced prompt gamma ray analysis, neutron activation analysis, and neutron reflective surface analysis disclosed in Patent Literature 1, but is a technology of measuring neutrons generated through a nuclear fission reaction caused by neutron irradiation.

Advantageous Effects of Invention

In the present invention, a reactor noise analysis process of excluding, from time series data obtained through detection of neutrons, data of a time range estimated to be largely affected by the primary neutrons generated in a pulsatile manner, is performed. Thus, processing based on data that is less affected by the primary neutrons becomes possible. As a result, the capability to detect a nuclear material can be enhanced, and it becomes possible to obtain a nuclear material detection device and a nuclear material detection method, which can be put to practical use.

BRIEF DESCRIPTION OF THE DRAWINGS

FIG. 7 contains graphs showing Y values obtained by the processing section through statistical processing.

FIG. 13 is a graph showing Y values obtained by the processing section through statistical processing (when signals from multiple detectors are used).

FIG. 14 is a graph showing a wave-height distribution obtained when neutrons, generated from the neutron source through a DD fusion reaction, are measured using a liquid scintillator.

DESCRIPTION OF EMBODIMENTS

In the following, embodiments of the present invention will be described based on the drawings.

1. Overall Configuration of Nuclear Material Detection Device

Figure 1:
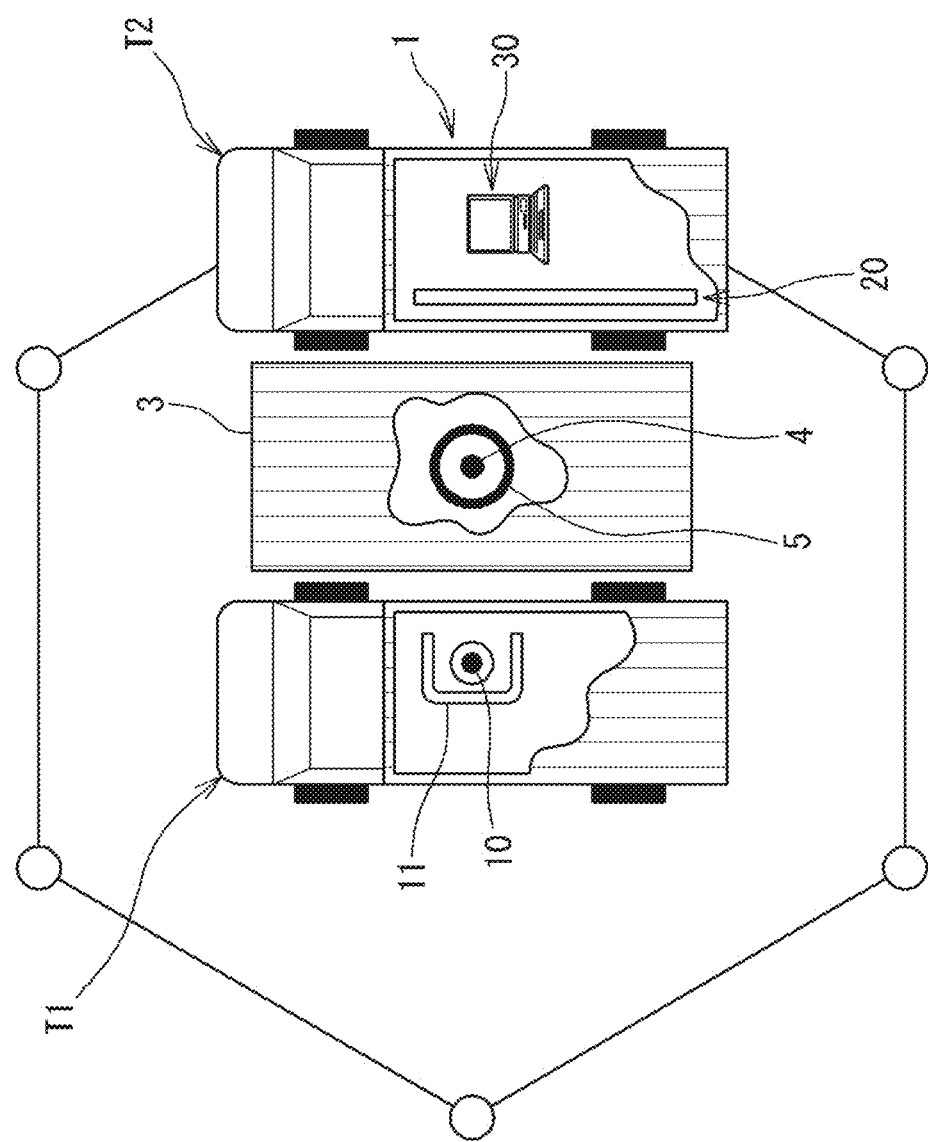
FIG. 1 is a plan view showing one embodiment of a nuclear material detection device of the present invention.

FIG. 1 is a plan view showing one embodiment of a nuclear material detection device 1 of the present invention. The nuclear material detection device 1 (hereinafter, also referred simply as a detection device 1) is a device configured to detect, using generated neutrons, a nuclear material (special nuclear material) 4 possibly concealed within a container 3 which is an object for inspection. For example, in mid-course of a distribution route of the container 3, the nuclear material 4 such as uranium-235 or plutonium-239 concealed within the container 3 is to be detected by the detection device 1. FIG. 1 shows a situation in which 1 kg of uranium-235, covered with a shield material (2-cm thick iron) 5 for making detection difficult, is concealed within the container 3.

The detection device 1 of the present embodiment can be mounted on a vehicle, and is a device that causes small harm in terms of radioactive contamination even when, by any remote chance, an accident occurs. Thus, the detection device 1 is small-sized to be mountable on a cargo bed of an automobile such as a truck, and has a neutron source 10 configured to generate neutrons. The neutron source 10 generates neutrons using a fusion reaction of reacting two deuterium atoms (hereinafter, referred to as DD fusion reaction).

The detection device 1 includes the neutron source 10 configured to generate neutrons used for irradiating the container 3, a detection section 20 that can detect neutrons, and a processing section 30 configured to perform data processing based on data obtained through detecting of neutrons by the detection section 20. The detection device 1 further includes a collimator (shield body) 11 to efficiently irradiate the container 3 with the generated neutrons.

In the present embodiment, the neutron source 10 and the collimator 11 are mounted on a cargo bed of a first automobile (truck) T1, and the detection section 20 and the processing section 30 are mounted on a cargo bed of a second automobile (truck) T2.

The automobiles T1 and T2 stop at a position near the container 3 such that the neutron source 10 and the detection section 20 are located adjacent to the container 3 that is possibly concealing the nuclear material 4.

Then, a range of approximately 5 meters in radius is set as off limits for avoiding exposure by neutron rays generated from the neutron source 10, the neutron source 10 is started up, and measurement of neutrons is performed by the detection section 20 while the container 3 is irradiated with neutrons. The presence of 1 kg of uranium-235 concealed within the container 3 is detected in an inspection time of approximately 10 minutes.

Figure 2:
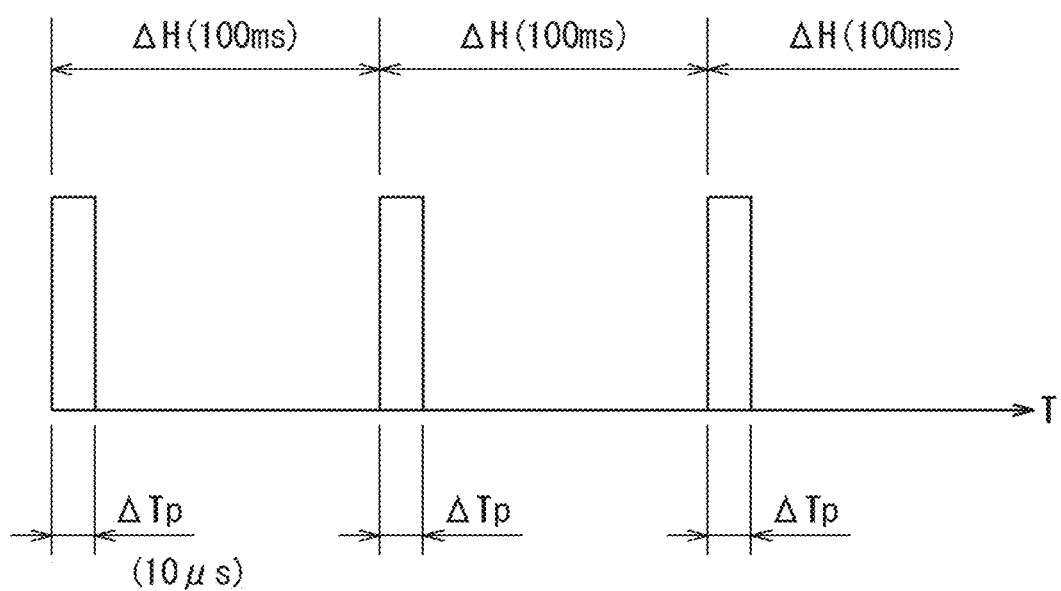
FIG. 2 is an illustrative diagram for describing a function of a neutron source.

FIG. 2 is an illustrative diagram for describing a function of the neutron source 10. As shown in FIG. 2, the neutron source 10 generates neutrons in a pulsatile manner in every predetermined time ΔH through the DD fusion reaction. The predetermined time ΔH is a pulse cycle, and this cycle can be set from 50 milliseconds to 1 second (resulting in a generation cycle from 20 Hz to 1 Hz). In the present embodiment, neutrons are generated in an interval of 100 milliseconds. Time ΔTp during which the neutrons are generated can be set from 5 to 50 microseconds, and is set to 10 microseconds in the present embodiment. The generation time ΔTp of the neutrons matches an irradiation time of the neutrons from the neutron source 10. It should be noted that the pulsatile manner may be, other than the pulsatile manner with rectangular waves, a pulsatile manner with delta waves or the like.

The neutron source 10 generates neutrons by, for example, generating plasma in a spherical container whose diameter is several tens of centimeters and which is filled with deuterium gas to cause a fusion reaction (DD fusion reaction) shown in the next formula (1).

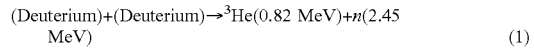
(Deuterium)+(Deuterium)→$^3$He(0.82 MeV)+$n$(2.45 MeV)   (1)

When the neutron source 10 is configured based on a fusion reaction between deuterium and tritium (DT fusion reaction), plasma is generated in a similar spherical container filled with a mixed gas of deuterium and tritium. With this, neutrons are generated by causing a fusion reaction shown in the next formula (2).

(Deuterium)+(Tritium)→$^4$He(3.67 MeV)+$n$(14.06 MeV)   (2)

It should be noted that those in the parentheses on the right side of each of the formulae (1) and (2) represent kinetic energies of each particle generated through the fusion reactions. These energies are determined based on energy conservation and momentum conservation before and after the reactions. In the DD fusion reaction in formula (1), a 2.45 MeV monoenergetic neutron ("n" in the formula) is generated; whereas, in the DT fusion reaction in formula (2), a 14.06 MeV monoenergetic neutron ("n" in the formula) is generated.

The detection section 20 can detect neutrons, and these neutrons include neutrons (referred to as primary neutrons) emitted from the neutron source 10, and, when the nuclear material 4 is concealed within the container 3, neutrons (referred to as secondary neutrons) generated through a nuclear fission reaction of the nuclear material 4. It should be noted that, in the nuclear material 4, other than the nuclear fission reaction caused by the primary neutrons, there are cases where a nuclear fission reaction is caused by the secondary neutrons generated from the nuclear fission reaction of the nuclear material 4.

The detection section 20 includes multiple detectors arranged side by side. As the detectors, various types can be employed. In addition, the detection section 20 can include multiple types of detectors. For example, the detection section 20 includes a helium-3 detector and an organic liquid scintillator. For a first detection process described in the following, the detection section 20 includes the helium-3 detector. For a second detection process described in the following, the detection section 20 includes the organic liquid scintillator.

The processing section 30 is formed of a computer having a processor (CPU), a storage device, and an input-output device. On the computer, a computer program for performing processes to detect a nuclear material based on data obtained through detection by the detection section 20 is installed. By executing the computer program, the computer functions as the processing section 30, and performs a process of generating predetermined data from output signals of the detection section 20, a reactor noise analysis process, and a neutron energy measurement process, which are described later.

2. Process by Processing Section 30

<2.1 Process of Generating Predetermined Data from Output Signals of Detection Section 20>

The neutrons detected by the detection section 20 (helium-3 detector) include not only the secondary neutrons generated through the nuclear fission reaction of the nuclear material, but also the primary neutrons emitted from the neutron source 10. When the detection section 20 detects such a neutron, the detection section 20 outputs a detection signal for that, and the processing section 30 acquires the detection signal, which is then processed to generate the predetermined data.

Figure 3:
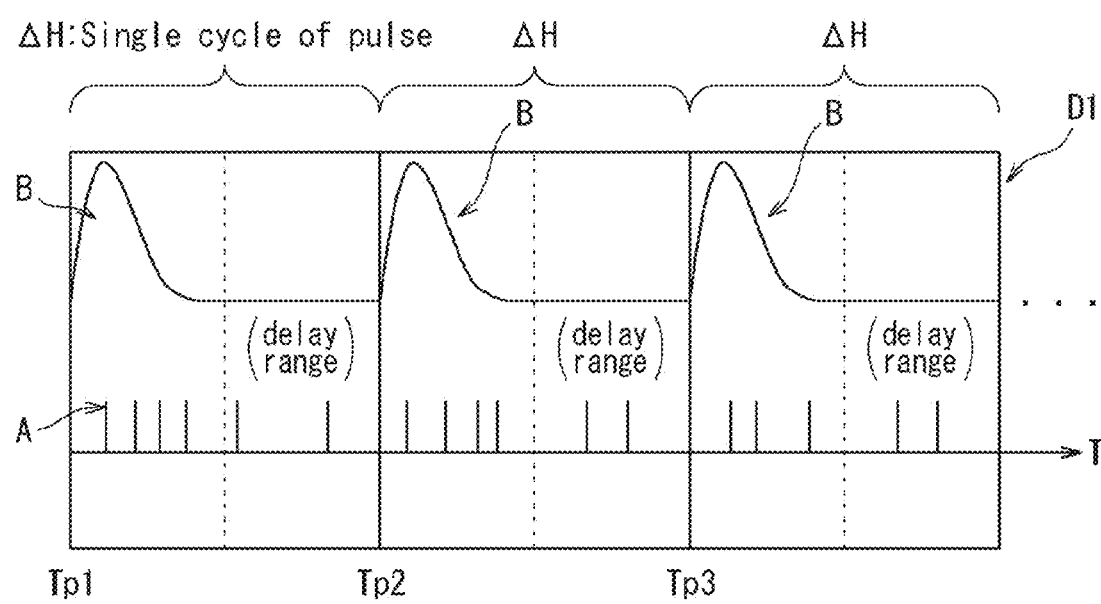
FIG. 3 is an illustrative diagram of data generated by a processing section.

FIG. 3 is an illustrative diagram of the data generated by the processing section 30. In FIG. 3, the horizontal axis represents time T, and the vertical axis represents a detection result of neutrons detected by the detection section 20. To describe specifically, when a secondary neutron reaches the detection section 20, the detection section 20 outputs a signal to the processing section 30. Thus, when a single secondary neutron reaches the detection section 20, the processing section 30 indicates a single count shown by an arrow A in FIG. 3. In a single cycle of neutron pulse generation from time Tp1 to Tp2 shown in FIG. 3, six secondary neutrons are counted.

A curve shown with an arrow B in FIG. 3 shows a counting rate of primary neutrons that have been emitted from the neutron source 10 and arrived at the detection section 20.

As shown in FIG. 2, when a neutron pulse is generated for every predetermined time $\Delta H$, the generated neutrons (primary neutrons) collide with, for example, various objects within the container 3 and are scattered or absorbed, and change in number. Thus, the temporal change of the counting rate of the primary neutrons arriving at the detection section 20 takes a curved shape shown by the arrow B in every single cycle of the pulse from time Tp1 to Tp2 shown in FIG. 3.

This curved shape will be described. The neutron source 10 generates a neutron pulse in every predetermined time $\Delta H$ (at a 10-Hz cycle). In FIG. 3, when a generation start timing (time of start of generation) of the neutron pulses is represented as Tpn (n=1, 2, 3, . . . ), the number (counting rate) of neutrons arriving at the detection section 20 reaches a peak in a time interval immediately after time Tpn. The number of neutrons exponentially reduces past this peak. Then, by repeatedly generating the neutron pulses from the neutron source 10, the curved shape representing the counting rate of the neutrons continues as shown in FIG. 3. As described above, the processing section 30 generates time series data D1 (cf. FIG. 3) shown in FIG. 3 from the signal outputted by the detection section 20 after detecting the neutrons (primary neutrons and secondary neutrons).

Figure 4:
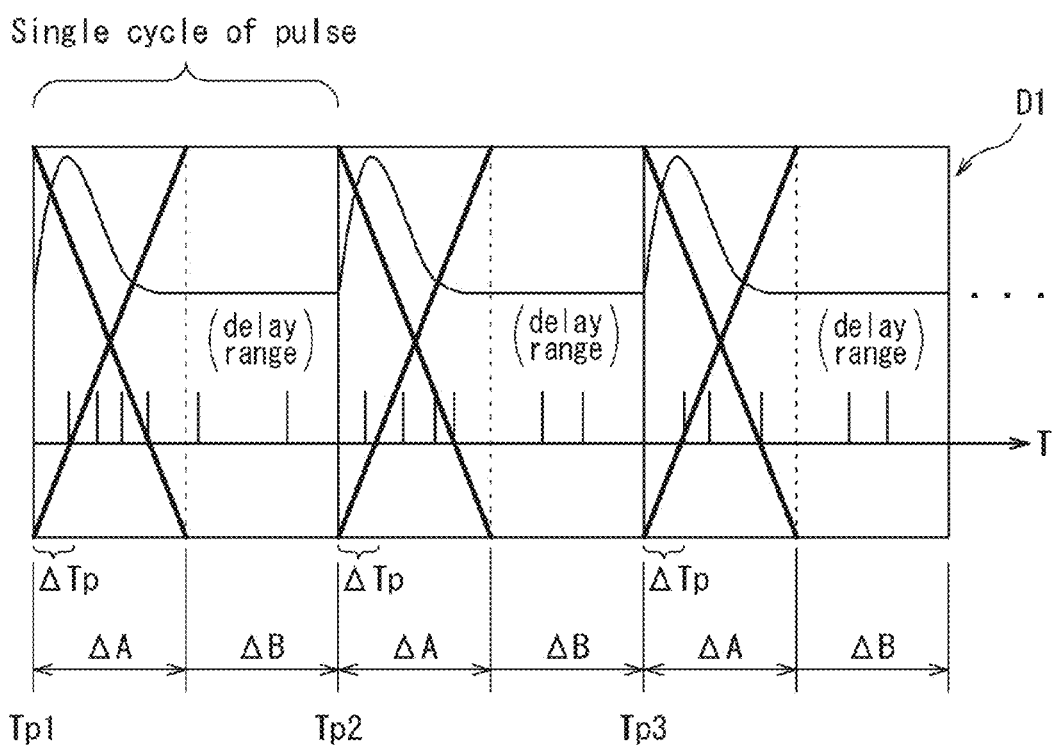
FIG. 4 is an illustrative diagram for describing a function of the processing section.

Furthermore, as shown in FIG. 4, the processing section 30 generates data obtained by excluding, from the time series data D1, data of a first time range $\Delta A$ including the generation time $\Delta Tp$ in which neutrons are generated by the neutron source 10 in the pulsatile manner. Time series data obtained by performing this process of excluding one portion of data is referred to as edited time series data D2 (cf. FIG. 5). The processing section 30 performs the reactor noise analysis process describe later, based on the edited time series data D2.

The processing section 30 defines, as the first time range $\Delta A$, an interval from the generation start timing Tpn (n=1, 2, 3, . . . ) of the neutrons generated by the neutron source 10 in the pulsatile manner to a timing after elapsing of a time period 500 to 5000 times of the generation time $\Delta Tp$ of the neutrons, and performs a process of excluding the data of the first time range $\Delta A$ from the time series data D1.

In the present embodiment, the generation time $\Delta Tp$ of the neutrons is 10 microseconds, and 5000 times thereof, i.e., 50 milliseconds, is the first time range $\Delta A$.

As shown in FIG. 4, the time range included in a single cycle of the neutron pulses generated by the neutron source 10 includes the first time range $\Delta A$ including the generation time $\Delta Tp$ of the neutron pulses and a second time range $\Delta B$ thereafter. Since the generation cycle of the neutron pulses is 10 Hz (an interval of 100 milliseconds), when the first time range $\Delta A$ is 50 milliseconds, the second time range $\Delta B$ is the remaining 50 milliseconds.

Data obtained by arranging the remaining data of the second time range $\Delta B$ in chronological order becomes the edited time series data D2. Thus, the edited time series data D2 (cf. FIG. 5) consists of data formed of continuous data of the second time range B.

Figure 5:
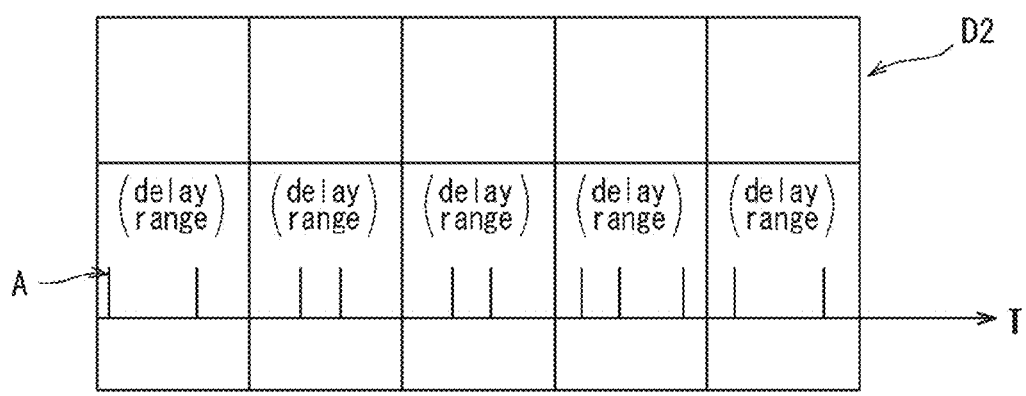
FIG. 5 is an illustrative diagram of data generated by the processing section.

As shown in FIGS. 4 and 5, the processing section 30, in addition to generating the time series data D1, extracts the data of the second time range $\Delta B$ obtained by excluding the data of the first time range $\Delta A$ from the time series data D1 in every generation cycle of the neutrons of the neutron source 10, and performs the later described reactor noise analysis process based on the extracted data (edited time series data D2).

With this, the processing section 30 performs the process based on a distribution (neutron noise) of the counting rate of the neutrons in the second time interval $\Delta B$ after the counting rate of the primary neutrons is lowered to a certain degree.

In the neutrons detected by the detection section 20 in the first time range $\Delta A$, prompt neutrons generated immediately after a pulsed neutron irradiation by the neutron source 10 are dominant; whereas in the neutrons detected by the detection section 20 in the second time range $\Delta B$, delayed neutrons generated in a delayed manner from the pulsed neutron irradiation by the neutron source 10 are dominant. Thus, the second time range $\Delta B$ is also referred to as a delay range.

<2.2 Reactor Noise Analysis Process>

The processing section 30 performs the reactor noise analysis process based on the edited time series data D2 shown in FIG. 5, and obtains a noise component (Y value). Then, the processing section 30 determines whether or not the noise component (Y value) is larger than a necessary value (threshold), and, when determined to be larger, determines that the nuclear material 4 is concealed within the container 3.

The noise component (Y value) is obtained by the next formula (3).

$$Y = ((\text{Variance of Count})/(\text{Average of Count})) - 1 \tag{3}$$

Thus, with regard to the edited time series data D2 generated by performing the detection of neutron by the detection section 20 for a necessary time period (e.g., 5 minutes) from the generation start of the neutron pulses at the beginning; the count within a certain gate width is counted, the average of the count and the variance of the count in the count obtained in the necessary time period are obtained, and a quantity (noise component) referred to as the Y value of the reactor noise analysis is obtained based on the average and the variance.

Then, a similar process as described above is performed after changing the gate width. As a result of this process, graphs (A) and (B) in FIG. 7 described in the following specific example are obtained. In the present embodiment, since data from an interval of 50 milliseconds of the second time range ΔB after elapsing of 50 milliseconds, to 100 milliseconds, subsequent to the generation of a neutron pulse in each cycle of neutron pulses, is analyzed as a single bundle, the maximum value of the gate width is 50 milliseconds.

The technology utilized by the detection device 1 for detecting the nuclear material 4 is a technology of measuring neutrons generated through the nuclear fission reaction caused by neutron irradiation. Thus, even when the nuclear material 4 is concealed within the container 3, since a chain reaction of nuclear fission occurs in the nuclear material 4 and neutrons detected therefrom deviate from Poisson distribution, the presence of the nuclear material 4 can be investigated by obtaining the Y value which is the level of the deviation.

<2.3 Specific Example of Reactor Noise Analysis Process>

A specific example of generation processes of the time series data D1 and the edited time series data D2, and neutron noise measurement including the reactor noise analysis process will be described.

Figure 6:
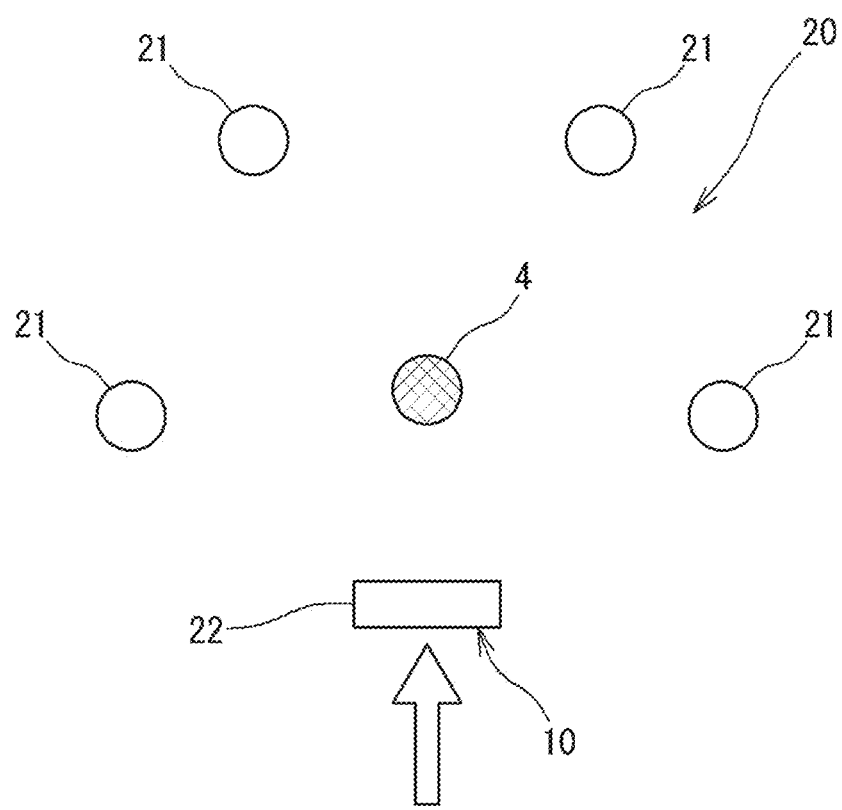
FIG. 6 is an illustrative diagram showing a schematic configuration of an experiment device.

FIG. 6 is an illustrative diagram showing a schematic configuration of an experiment device for the specific example. It should be noted that in the experiment device, the neutron source 10 is configured to generate neutrons not through the DD fusion reaction but through the fusion reaction of deuterium and tritium (hereinafter, also referred to as DT fusion reaction).

With respect to a tritium target 22, a deuterium ion beam is directed in a pulsatile manner, and neutrons are generated through the DT fusion reaction. A neutron generation rate at the tritium target 22 which is a generation point is $10^8$ neutrons/second in average.

While irradiating the highly enriched uranium (the nuclear material 4) with the neutrons generated from the neutron source 10 in the pulsatile manner, neutrons are detected by the detection section 20 having four helium-3 detectors 21.

Here, a neutron detection experiment was performed by the detection section 20 in three cases: a case of 0.5 kg and a case of 0.25 kg as the amount of the highly enriched uranium (the nuclear material 4), and a case in which the highly enriched uranium (the nuclear material 4) did not exist. The time series data D1 with the counting rates of neutrons detected by the detection section 20 resulted in that shown in FIG. 3. From the time series data D1, the data of the second time range (delay range) ΔB, in which the delayed neutrons are dominant and that is less affected by the irradiation of the neutron pulses, was extracted (cf. FIG. 5). Then, the edited time series data D2 obtained by extracting the data of the second time range ΔB and arranging that in a chronological order was statistically processed by the processing section 30 to calculate the noise component referred to as the Y value.

In FIG. 7, (A) and (B) are graphs showing the Y values obtained by the processing section 30 through statistical processing. In FIG. 7, (A) shows the case in which the amount of the highly enriched uranium (the nuclear material 4) was 0.5 kg (arrow K1), and, as a comparison for that, the case in which the highly enriched uranium was not placed (arrow K0). The horizontal axis indicates a gate width. In FIG. 7, (B) shows the case in which the amount of the highly enriched uranium (the nuclear material 4) was 0.25 kg (arrow K2), and, as a comparison for that, the case in which the highly enriched uranium was not placed (arrow K0).

As shown in each of (A) and (B) of FIG. 7, the presence of the highly enriched uranium (the nuclear material 4) and the difference resulting from the amount thereof are clearly indicated in terms of the Y values.

With the present experimental condition, the presence of 0.25 kg of the highly enriched uranium (the nuclear material 4) can be detected in 10 minutes. Thus, for example, when the amount of uranium which is the nuclear material 4 in the embodiment shown in FIG. 1 is 1 kg, the amount of uranium in the embodiment shown in FIG. 1 is four times of the amount of uranium in the present experiment. Since the neutron generation rates by the neutron source 10 in the present experiment and in the embodiment shown in FIG. 1 are equally $10^8$ neutrons/second in average, the presence of the highly enriched uranium in the embodiment shown in FIG. 1 can be detected in a sufficiently practical time period by using the detection section 20 having, for example, the four helium-3 detectors 21 in the embodiment shown in FIG. 1.

It should be noted that although the detection section 20 includes the four helium-3 detectors 21 as described above, the graphs shown in (A) and (B) of FIG. 7 are graphs indicating Y values obtained through statistical processing of signals obtained from one of the four detectors 21. As in this case, although the Y values can be obtained from the signals obtained from a single detector 21, the Y values are more preferably obtained based on signals obtained from a plurality of detectors 21. For example, the graph shown in FIG. 13 shows Y values obtained through statistical processing of signals obtained from all the plurality of the detectors 21. The graph shown in FIG. 13 is similar to the graph shown in (A) of FIG. 7 in terms of showing the Y values obtained by the processing section 30 through statistical processing in the case in which the amount of the highly enriched uranium (the nuclear material 4) was 0.5 kg (arrow K1), and, as a comparison for that, the case in which the highly enriched uranium was not placed (arrow K0). However, the graph shown in FIG. 13 shows Y values obtained through statistical processing of signals from all nine detectors 21 included in the detection section 20.

In the case of FIG. 13, when compared to the case in (A) of FIG. 7, the difference between the presence and absence of the highly enriched uranium is more clearly shown. In particular, as obvious from the difference in the scale of the horizontal axes of the graphs shown in FIG. 13 and (A) of FIG. 7, the difference between the presence and absence of the highly enriched uranium appears in a shorter period of time in the case shown in FIG. 13. Thus, by obtaining Y values based on signals obtained from the plurality of the detectors 21, the presence or absence of the highly enriched uranium can be detected more clearly in a shorter period of time. In such manner, by increasing the number of the detectors 21 included in the detection section 20 and using signals obtained from these detectors 21, the difference between the presence and absence of the highly enriched uranium observed as the Y value can be clarified further, and the difference can be determined in a shorter period of time.

<2.4 Regarding Detection Device for Performing Neutron Noise Measurement Including Reactor Noise Analysis Process>

The neutrons detected by the detection section 20 include the primary neutrons emitted from the neutron source 10, and, when the nuclear material 4 is concealed within the container 3, the secondary neutrons generated through the nuclear fission reaction of the nuclear material 4. Although detection of the secondary neutrons is necessary for detecting the presence of the nuclear material 4, the detection of the secondary neutrons sometimes becomes difficult because of the effect of the primary neutrons. More specifically, the primary neutrons become the background to cause the detection of the secondary neutrons to be difficult.

However, in the detection device 1 according to the present embodiment, the neutrons (primary neutrons) are generated from the neutron source 10 in the pulsatile manner, and the reactor noise analysis process is performed after excluding the data of the first time range $\Delta A$ that is estimated to be largely affected by the primary neutrons, from the time series data D1 obtained through detection of neutrons by the detection section 20. Thus, the processing section 30 performs the reactor noise analysis process based on the edited time series data D2 less affected by the primary neutrons.

The noise component (Y value) is obtained by: excluding, from the time series data D1, the data of the first time range $\Delta A$ that is largely affected by the primary neutrons generated by the neutron source 10 in the pulsatile manner; extracting the data of the second time range $\Delta B$ that is less affected by the primary neutrons; and performing the reactor noise analysis process based on the edited time series data D2, which has been extracted, of the second time range $\Delta B$.

With the reactor noise analysis process, since a characteristic tendency associated with a chain reaction of nuclear fission in the nuclear material 4 can be captured, the nuclear material 4 can be detected even in the presence of the emitted neutrons which become the background. Thus, since the difference between the presence and absence of the nuclear material 4 appears more clearly regarding the Y value, the capability to detect the nuclear material 4 can be enhanced, and a nuclear material detection device that can be put to practical use can be obtained.

As in the embodiment described above (cf. FIG. 4), the processing section 30 defines, as the first time range $\Delta A$, an interval from the generation start timing (e.g., time Tp1) of the neutron pulses from the neutron source 10 to a timing after elapsing of a time period 500 to 5000 times of the generation time $\Delta Tp$ of the neutrons, and excludes the data of the first time range $\Delta A$ from the time series data D1. As a result, the effect of the primary neutrons generated by the neutron source 10 in the pulsatile manner can be effectively excluded, and statistical error in the reactor noise analysis process can be reduced by reducing the amount of data excluded from the time series data D1 as much as possible.

Furthermore, in the experiment described above, although the DT fusion reaction is used as the neutron source, the neutron source 10 in the detection device 1 shown in FIG. 1 uses the DD fusion reaction. When compared to the DT fusion reaction, although the DD fusion reaction is inferior in terms of the amount of the neutrons generated, the nuclear material 4 that is concealed can be detected even when the DD fusion reaction is used as the neutron source 10, since the capability to detect the nuclear material 4 can be enhanced because of the functions of the detection section 20 and the processing section 30. Furthermore, since tritium is not used in the DD fusion reaction, the device is safe and can be easily handled.

In particular, although the neutron source 10 is mounted on the automobile T1 (movable body that moves with respect to a road surface) as shown in FIG. 1, since the DD fusion reaction is used, a clean device having a small possibility of radioactive contamination even when, by any remote chance, an accident occurs can be obtained.

Furthermore, in order to mount the neutron source 10 on the automobile T1, it is necessary to reduce the size of the neutron source 10. With the detection device 1 of the present embodiment, since the capability to detect the nuclear material 4 can be enhanced as described above, a small size neutron source is sufficient instead of a large size neutron source for generating a large amount of neutrons. As a result, mounting of the neutron source 10 on the automobile T1 becomes possible. In addition, since the capability to detect the nuclear material 4 can be enhanced, the number of the detector(s) 21 can be reduced to a necessary minimum, and the overall size of the detection section 20 can be reduced, enabling mounting of the detection section 20 on the automobile T2.

<2.5 Neutron Energy Measurement Process>

Besides detecting the nuclear material 4 based on the reactor noise analysis process, the detection device 1 shown in FIG. 1 can also detect the nuclear material 4 based on a neutron energy measurement.

For this purpose, the neutron source 10 generates 2.45 MeV neutrons using the DD fusion reaction of reacting two deuterium atoms. The neutron generation rate from this neutron source 10 is $10^8$ neutrons/second in average.

In addition, the detection section 20 has a function of detecting a neutron together with an energy thereof. For example, the detection section 20 includes a detector 21 having an organic liquid scintillator. The processing section 30 can, based on a detection signal from this detector 21, obtain an energy spectrum of the neutron.

As shown in formula (2), when the DT fusion reaction is used, since neutrons having a high energy of 14.06 MeV are generated, neutrons having an energy of 14.06 MeV at maximum exist even when the energy is reduced using a moderator. When the container 3 is irradiated with these neutrons to induce nuclear fission in the nuclear material 4 concealed within the container 3 and the released neutrons (secondary neutron) associated with the nuclear fission are measured, an average of the energy is approximately 2 MeV and is lower than 14.06 MeV.

Thus, when the neutrons (secondary neutrons) generated by the nuclear fission of the nuclear material 4 is measured, the neutrons (primary neutrons) emitted at the beginning may be detected by the detection section 20, and these neutrons (primary neutrons) become a background. This background occurs fundamentally since the energy of the neutrons generated in the DT fusion reaction is as high as 14.06 MeV.

Thus, in the present embodiment, the DD fusion reaction shown in formula (1) is utilized.

Figure 8:
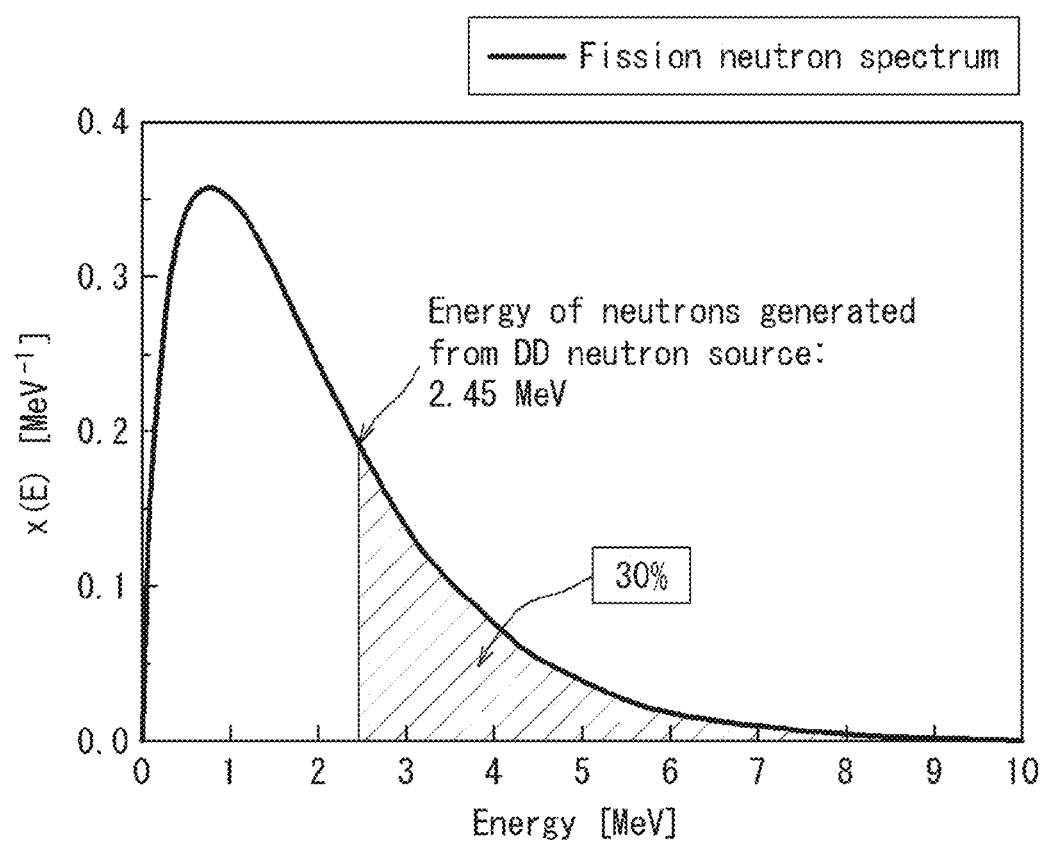
FIG. 8 is an illustrative diagram of energy of neutrons.

When the DD fusion reaction is used, the maximum energy of the neutrons that have been generated by the neutron source 10 and have reached the detection section 20 is 2.45 MeV. In the secondary neutrons generated through the nuclear fission in the nuclear material 4 that is to be detected, components having an energy higher than 2.45 MeV account for approximately 30% of the total secondary neutrons as shown in FIG. 8. For this reason, when a configuration for detecting a neutron having an energy higher than 2.45 MeV by the detection section 20 and the processing section 30 is used, the emitted neutrons do not fundamentally become a background.

Thus, the processing section 30 of the detection device 1 according to the present embodiment shown in FIG. 1 has a function of determining that the neutrons detected by the detection section 20 include a neutron having an energy higher than the maximum energy (i.e., 2.45 MeV) of the neutrons that have been generated through the DD fusion reaction and have reached the detection section 20. In such manner, among the secondary neutrons generated by the nuclear fission reaction induced in the nuclear material 4 when being irradiated by the neutrons from the neutron source 10, components having an energy higher than 2.45 MeV are measured by the processing section 30.

By setting, as a target to be detected, the neutron having an energy higher than the maximum energy (2.45 MeV) of the neutrons generated through the DD fusion reaction, the primary neutrons do not become a background, and the processing section 30 can determine that the nuclear material 4 exists when a neutron having an energy higher than the maximum energy (2.45 MeV) is detected. Thus, with DD fusion reaction, when the nuclear material 4 does not exist within the container 3, only the neutrons whose energy is equal to or lower than 2.45 MeV should be detected by the detection section 20. On the other hand, when neutrons whose energy is equal to or higher than 2.45 MeV are detected, it can be determined that the nuclear material 4 exists within the container 3.

In addition, with the detection device 1 shown in FIG. 1, since it is not necessary to select for neutrons that are to be emitted in accordance with their energy, and it is possible to provide contribution to size-reduction by not using, for example, a neutron wavelength separation device and a neutron guide tube.

Furthermore, by using a discharge type fusion device of the present embodiment as the neutron source 10, a small size device that can be mounted on an automobile such as a truck can be achieved, and a necessary neutron strength can be obtained. In addition, since tritium is not used, the risk of radioactive contamination in the public is small, and the device can be suitably used for a detection device that can be moved in an automobile or the like.

<2.6 Specific Example of Neutron Energy Measurement>

Figure 9:
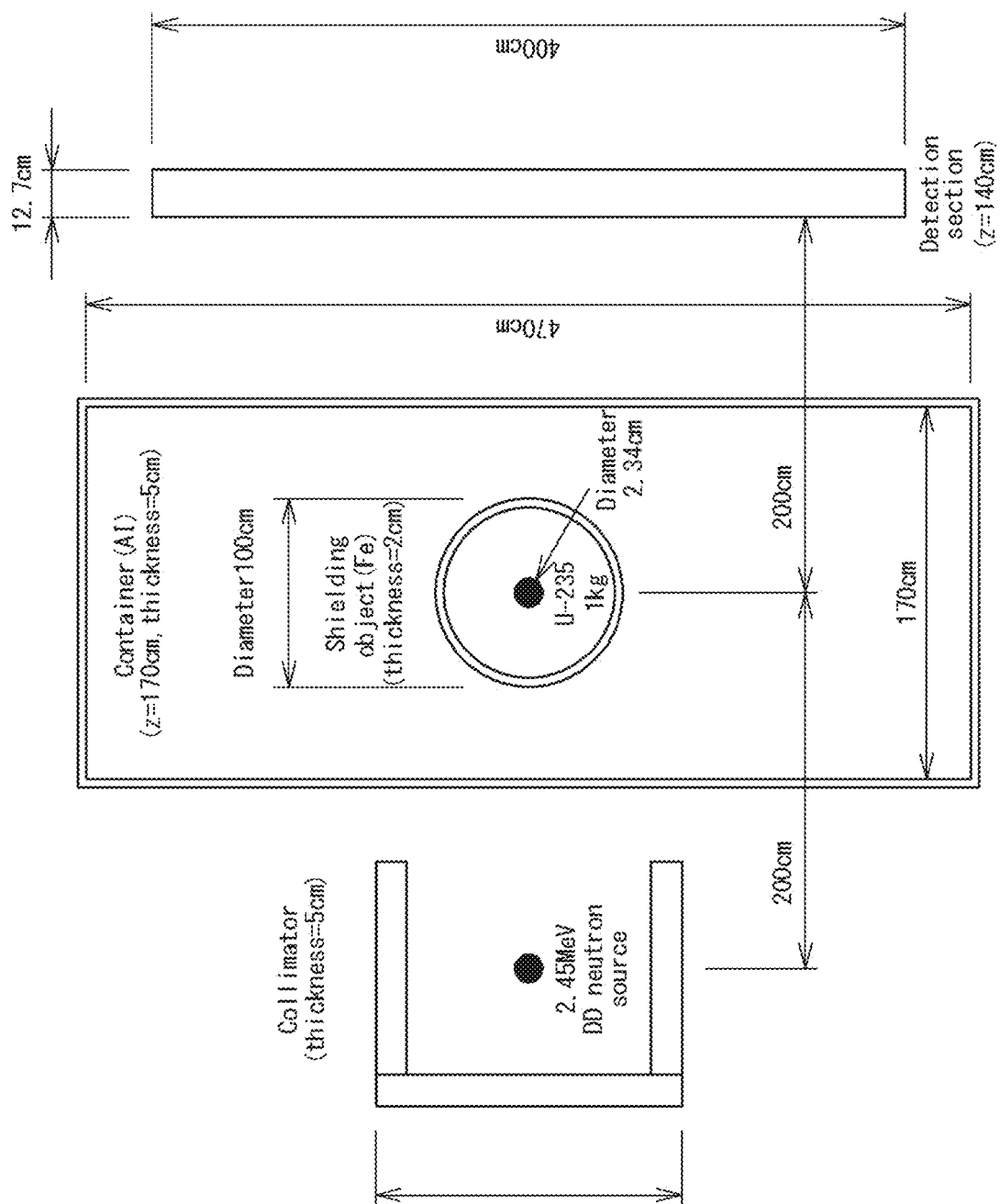
FIG. 9 is an illustrative diagram showing a computational architecture for a simulation of neutron energy measurement.

A specific example of the neutron energy measurement by the detection device 1 in FIG. 1 will be described. A numerical simulation of the neutron energy measurement was performed using the continuous energy Monte Carlo calculation code MCNP envisioning the embodiment shown in FIG. 1. The computational architecture is shown in FIG. 9. As a nuclear data library, JENDL3.3 was used. 1 kg of uranium-235 was placed in the center of spherical shielding object made from a 2-cm thick iron, and the shielding object was placed in a general shipping container (20'×8'×8').

The neutron source by the DD fusion reaction was a 2.45 MeV point radiation source, and a polyethylene collimator having a thickness of 5 cm and a width (diameter) of 130 cm was disposed therearound. In this simulation, a neutron moderator was not used. Using an arrangement of each device shown in FIG. 9, neutron energy spectra at the detection section and an elastic scattering reaction rate between a hydrogen nucleus and a neutron in the organic liquid scintillator were obtained.

Figure 10:
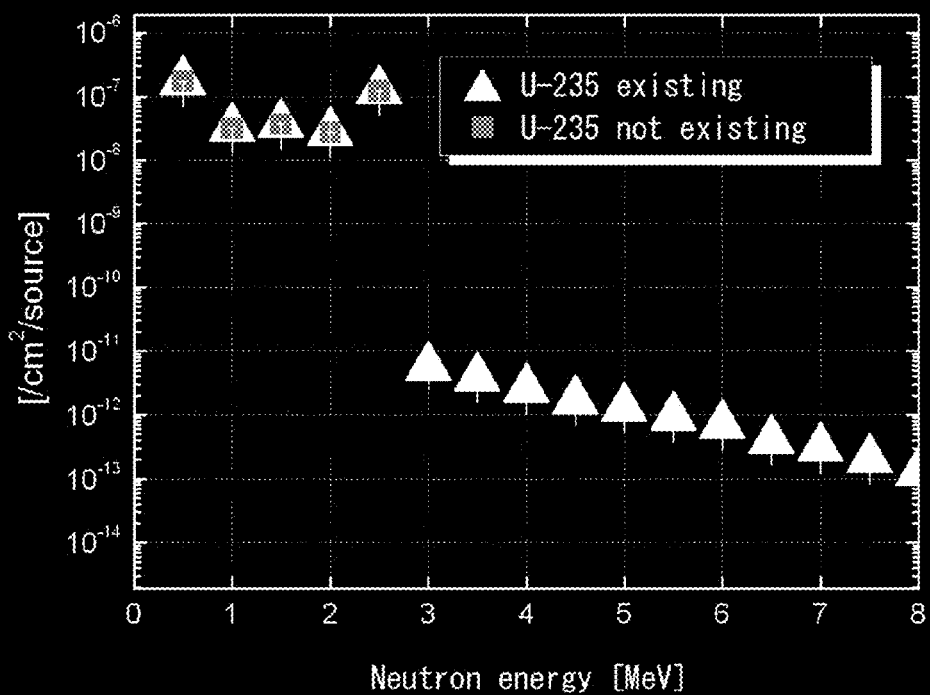
FIG. 10 is a graph showing energy spectra of neutrons detected by a detection section.

The energy spectra of neutrons detected by the detection section are shown in FIG. 10. A case in which uranium-235 did not exist is indicated by square points, and, as shown in FIG. 10, a neutron whose energy is equal to or higher than 2.45 MeV does not exist. On the other hand, in a case in which uranium-235 did exist (triangular points), a neutron energy spectrum exceeding 2.45 MeV caused by induced nuclear fission reaction is clearly observed. From the result of the reaction rate obtained through the calculation, the counting rate of neutrons whose energy is equal to or higher than 2.45 MeV was 56 cps.

Here, the graph shown in FIG. 14 shows a result of experimentally measuring, in the absence of highly enriched uranium, a neutron energy spectrum by the detection section 20 using a neutron source by the DD fusion reaction and an organic liquid scintillator as the detector. Thus, FIG. 14 shows a background evaluation in the absence of highly enriched uranium. In the graph shown in FIG. 14, each dot represents a measurement result, and a solid line L represents the result of a simulation (calculated value of an incidence 2.45 MeV monochromatic neutron) of neutrons generated by the DD fusion reaction. Thus, a high energy area (area equal to or greater than 0.8 of the horizontal axis in the graph of FIG. 14) that is short of the solid line L is the area of interest equal to or higher than 2.45 MeV. The result shown in FIG. 14 shows that, with respect to the total counting rate of approximately 1000 cps including the neutrons from the DD fusion reaction and other radiation, a background signal appearing in the area equal to or higher than 2.45 MeV was approximately 2 cps.

In the numerical simulation whose computational architecture is shown in FIG. 9, among the secondary neutrons generated from uranium-235, a measured total neutron counting rate was approximately 200 cps. Among that, a counting rate of the secondary neutrons whose energy is equal to or higher than 2.45 MeV which is the maximum energy of the emitted neutrons was approximately 60 cps.

Since the background signal was very small as approximately 2 cps even when the total counting rate was as high as approximately 1000 cps in the measurement experiment (cf. FIG. 14) absent of uranium, overcoming the background signal can be expected sufficiently when uranium exists even when statistical error is taken into consideration. Thus, in the embodiment shown in FIG. 1, the presence of 1 kg of uranium-235 can be detected in an inspection time of approximately 10 minutes.

3. Regarding Detection of Nuclear Material 4 through Reactor Noise Analysis Process and Detection of Nuclear Material through Neutron Energy Measurement In the present embodiment, it is possible to parallelly perform the detection (first detection process) of the nuclear material 4 through the reactor noise analysis process, and the detection (second detection process) of the nuclear material based on detection of a neutron having an energy higher than 2.45 MeV. In this case, the reliability of detecting the nuclear material improves, since one of the detection processes functions as a backup of the other detection process, and the other detection process functions as a backup of the one of the detection processes.

Thus, in the case where the nuclear material 4 is concealed within the container 3, even if the existence of the nuclear material 4 is denied by a false detection in the first detection process, the container 3 is inspected in further detail when the existence of the nuclear material is affirmed in the second detection process, and the concealed nuclear material 4 can be discovered without being overlooked.

It should be noted that, by using one of the first detection process and the second detection process instead of using both, the problem in conventional art is solved, and necessary capabilities for a nuclear material detection device that can be put to practical use are obtained.

Specifically, the detection device 1 having a function of performing only the second detection process is as described in the following.

The nuclear material detection device 1 for detecting the nuclear material 4 possibly concealed within an object (container 3), the nuclear material detection device 1 including:

the neutron source 10 configured to generate, using a fusion reaction of reacting two deuterium atoms, neutrons used for irradiating the object;

the detection section 20 capable of detecting neutrons, together with an energy thereof, including primary neutrons emitted from the neutron source 10 and secondary neutrons generated through a nuclear fission reaction of the nuclear material; and the processing section 30 configured to perform a process based on data obtained through detecting of neutrons by the detection section 20, wherein the processing section 30 performs a process of determining that the neutrons detected by the detection section 20 include a neutron having an energy higher than a maximum energy of the neutrons that have been generated through the fusion reaction and have reached the detection section 20.

With the detection device 1 having a function of performing only the second detection process, when neutrons are generated from the neutron source 10 using the fusion reaction of reacting two deuterium atoms (DD fusion reaction), the maximum energy of the primary neutrons reaching the detection section 20 takes a certain value (2.45 MeV). On the other hand, the secondary neutrons generated from the nuclear material 4 that is to be detected include a large amount of neutrons having an energy higher than the certain value (2.45 MeV). Thus, by setting, as a detection target, the neutrons having an energy higher than the maximum energy of the neutrons generated through the DD fusion reaction, the primary neutrons do not become a background, and the nuclear material can be determined to exist when a neutron having an energy higher than the maximum energy is detected.

It should be noted that, when detecting (second detection process) the nuclear material by the neutron energy measurement, although the neutron source 10 may generate the neutrons in the pulsatile manner, the neutrons may be generated steadily instead of in the pulsatile manner.

4. Modification

Although the embodiment shown in FIG. 1 describes a case in which the neutron source 10 and the detection section 20 are each mounted on an automobile, other than that, at least one of the neutron source 10 and the detection section 20 may be mounted on an automobile. Furthermore, the automobile may be one that is not a truck, and may be an automobile specialized for the detection device 1. Further, although the movable body having mounted therein at least one of the neutron source 10 and the detection section 20 and moving with respect to a road surface has been described to be an automobile, the movable body may be one that is not an automobile.

Figure 11:
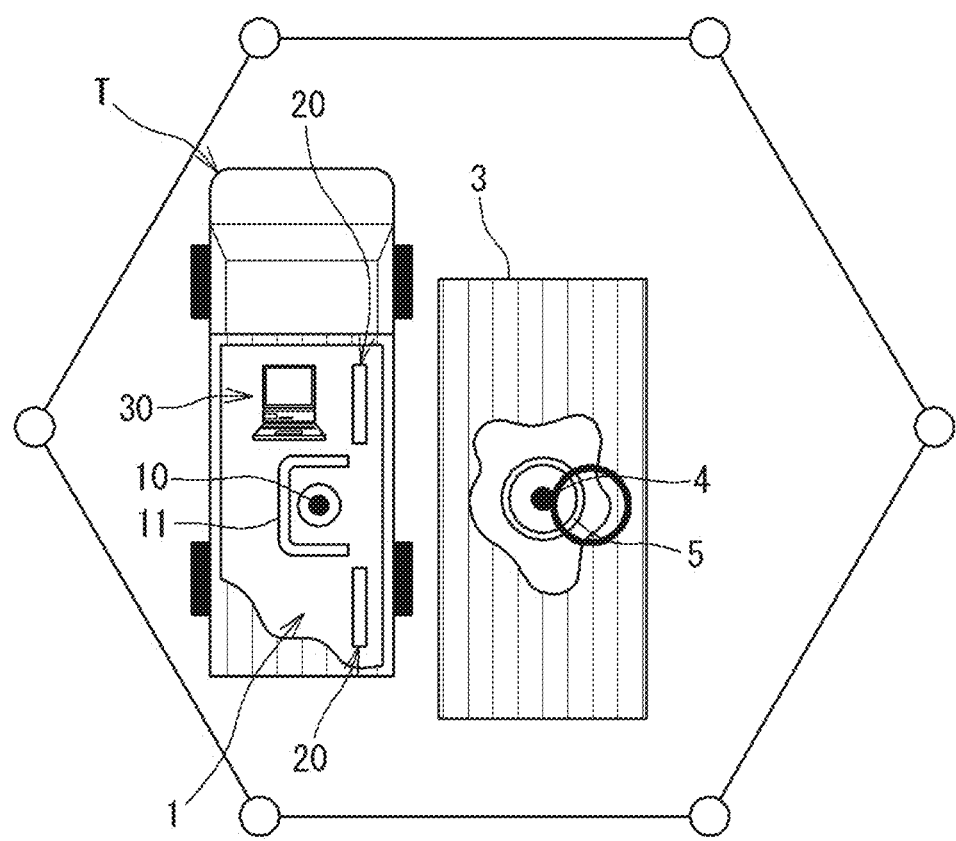
FIG. 11 is a plan view showing a modification of the nuclear material detection device.

Furthermore, in the embodiment described above (FIG. 1), a case has been described in which there are two automobiles, and the neutron source 10 and the detection section 20 are separately mounted on the automobiles T1 and T2, respectively. However, as shown in FIG. 11, there may be a single automobile T (movable body), and this automobile may have both the neutron source 10 and the detection section 20 mounted thereon. In FIG. 11, two detection sections 20 are provided such that the neutron source 10 is interposed between the detection sections 20.

Furthermore, in the embodiment shown in FIG. 1, a case has been described in which, the first automobile T1 having mounted thereon the small sized neutron source 10 and neutron collimator 11, and the second automobile T2 having mounted thereon the detection section 20 for the neutron noise measurement and the energetic neutron measurement, are parked at positions flanking the container 3 from both sides. In this case, an irradiation direction of the neutrons from the neutron source 10 toward the container 3 is included in a detection direction, which is from the container 3 toward the detection section 20, for the neutrons originating from the nuclear material 4 in the detection section 20.

However, instead of this embodiment, the irradiation direction of the neutrons from the neutron source 10 toward the container 3, and the detection direction of the neutrons from the container 3 toward the detection section 20, are preferably in an intersecting relationship.

Figure 12:
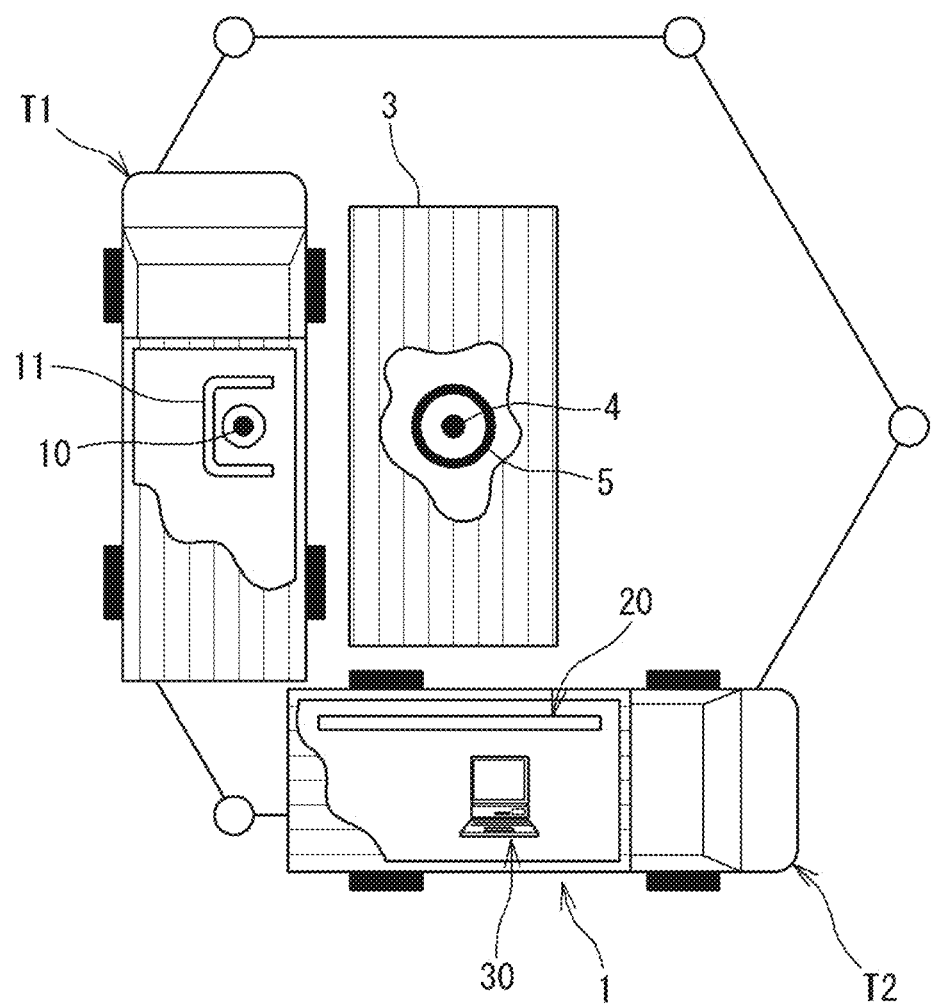
FIG. 12 is a plan view showing still another modification of the nuclear material detection device.

For example, as shown in FIG. 12, preferably, the neutron source 10 is disposed so as to face one surface of the container 3 formed cubically, and the detection section 20 is disposed so as to face another surface of the container 3. In this case, the primary neutrons emitted in a direction from the neutron source 10 toward the container 3 can be prevented from directly irradiating the detection section 20, and the effect of the primary neutrons in the detection section 20 can be suppressed further effectively.

As shown in FIG. 11, when a single automobile T is used, the irradiation direction of the neutrons from the neutron source 10 toward the container 3 and the detection direction of the neutrons from the container 3 toward each of the detection sections 20 form a V-shape, and these directions intersect with each other.

Furthermore, the arrangement of the neutron source 10 and the detection section 20 may be a mode other than those shown in FIGS. 11 and 12, and, for example, although not diagrammatically represented, the detection section 20 may be disposed on top of the container 3.

In the embodiment and each of the modifications described above, since a neutron wavelength separation device for extracting neutrons having a specific wavelength among the generated neutrons, or a neutron guide tube for guiding the neutrons is not used; the emitted neutrons are radiated with respect to the container 3 not in a beam-like manner but in a broad range and thereby the volume that can be inspected becomes large, resulting in the detection device 1 that can be put to practical use, and it is also possible to provide contribution to size-reduction of the device.

The detection device 1 of the present invention is not limited to the mode diagrammatically represented, and may be in other modes without departing from the scope of the present invention. That is, the embodiments (including each of the modifications) disclosed herein are in all aspects illustrative and not restrictive. The scope of rights of the present invention is not limited to the embodiments described above, and includes all the configurations disclosed in the scope of the claims and all modifications within an equivalent scope.

REFERENCE SIGNS LIST 1 nuclear material detection device
3 container (object)
4 nuclear material
T1 automobile (movable body)
T2 automobile (movable body)
10 neutron source
20 detection section
30 processing section
ΔTp generation time
ΔH predetermined time
D1 time series data
ΔA first time range
ΔB second time range

What is claimed is:

1. A nuclear material detection device for detecting a nuclear material within an object, the nuclear material detection device comprising:
a neutron source configured to generate neutrons used for irradiating the object;
a detection section capable of detecting neutrons including primary neutrons emitted from the neutron source and secondary neutrons generated through a nuclear fission reaction of the nuclear material; and
a processing section configured to perform a reactor noise analysis process based on data obtained through detecting of neutrons by the detection section, wherein
the neutron source is configured to generate the primary neutrons in a pulsatile manner, wherein
the processing section is configured to obtain edited time series data by excluding data of a time range containing a generation time during which the neutron source generates the primary neutrons in the pulsatile manner, from time series data obtained by detecting the neutrons by the detection section, wherein
the processing section obtains a neuron count from the edited time series data; generates a noise component value based on a ratio of an average neutron counts and a variance of a neutron count; and when the noise component value is larger than a predetermined threshold, detects the nuclear material within the object.

2. The nuclear material detection device according to claim 1, wherein the processing section generates edited time series data and performs the reactor noise analysis process based on the edited time series data to obtain a noise component, and
wherein the time range is a time period of 500 to 5000 times the generation time of the primary neutrons.

3. The nuclear material detection device according to claim 1, wherein the time range is a time period of 500 to 5000 times the generation time of the primary neutrons.

4. The nuclear material detection device according to claim 1, wherein at least one of the neutron source and the detection section is configured to be mounted on a movable body that moves with respect to a road surface.

5. The nuclear material detection device according claim 2, wherein at least one of the neutron source and the detection section is configured to be mounted on a movable body that moves with respect to a road surface.

6. The nuclear material detection device according to claim 3, wherein at least one of the neutron source and the detection section is configured to be mounted on a movable body that moves with respect to a road surface.

7. The nuclear material detection device according to claim 2, wherein at least one of the neutron source and the detection section is configured to be mounted on a movable body that moves with respect to a road surface.

8. The nuclear material detection device according to claim 4, wherein a direction from the neutron source toward the object, and a direction from the object toward the detection section, are aligned in a non-coaxial manner to each other.

9. A nuclear material detection method for detecting a nuclear material within an object, the method comprising:
irradiating the object with neutrons in a pulsatile manner;
detecting neutrons including primary neutrons used for the irradiating and secondary neutrons generated through a nuclear fission reaction of the nuclear material;
performing a reactor noise analysis process based on data obtained through the detecting, the reactor noise analysis process being performed based on data obtained through exclusion of data of a time range that includes a generation time during which the primary neutrons are generated in the pulsatile manner, from time series data obtained through the detecting of neutrons;
obtaining edited time series data by excluding data of a time range containing a generation time during which the neutron source generates the primary neutrons in the pulsatile manner, from time series data obtained by detecting the neutrons by the detection section;
obtaining a neuron count from the edited time series data;
obtaining a noise component value based on a ratio of an average neutron counts and a variance of the neutron count; and
and when the noise component value is larger than a predetermined threshold, detecting the nuclear material within the object.

10. The nuclear material detection device according to claim 1, wherein the neutron source is configured to generate the neutrons using a fusion reaction of reacting two deuterium atoms by generating plasma in a container which is filled with deuterium gas.

11. The nuclear material detection device according to claim 2, wherein the neutron source is configured to generate the neutrons using a fusion reaction of reacting two deuterium atoms by generating plasma in a container which is filled with deuterium gas.

12. The nuclear material detection device according to claim 3, wherein the neutron source is configured to generate the neutrons using a fusion reaction of reacting two deuterium atoms by generating plasma in a container which is filled with deuterium gas.

13. The nuclear material detection device according to claim 1, wherein the neutron source and the object are configured in such a way that a direction from the neutron source toward the object, and a direction from the object toward the detection section intersect each other.

14. The nuclear material detection device according to claim 2, wherein the neutron source and the object are configured in such a way that a direction from the neutron source toward the object, and a direction from the object toward the detection section intersect each other.

15. The nuclear material detection device according to claim 3, wherein the neutron source and the object are configured in such a way that a direction from the neutron source toward the object, and a direction from the object toward the detection section intersect each other.

16. The nuclear material detection device according to claim 1, wherein:
- the neutron source is configured to generate the neutrons using a fusion reaction of reacting two deuterium atoms by generating plasma in a container which is filled with deuterium gas;
- the detection section has a function of detecting a neutron together with an energy thereof; and the processing section uses neurons having an energy higher than the maximum energy of the neutrons generated through the fusion reaction as targets to obtain the neuron count.

* * * * *